United States Patent [19]
Yoneda et al.

[11] Patent Number: 5,626,845
[45] Date of Patent: May 6, 1997

[54] METHOD TO AMELIORATE OSTEOLYSIS AND METASTASIS

[75] Inventors: Toshiyuki Yoneda; Gregory R. Mundy, both of San Antonio, Tex.

[73] Assignee: Xenotech Incorporated, Foster City, Calif.

[21] Appl. No.: 376,359

[22] Filed: Jan. 23, 1995

[51] Int. Cl.$^6$ .................................................. A61K 39/395
[52] U.S. Cl. ................................. 424/145.1; 424/158.1; 424/130.1; 514/885
[58] Field of Search ........................... 424/130.1, 138.1, 424/145.1, 158.1; 514/885

[56] References Cited

U.S. PATENT DOCUMENTS

| | | | |
|---|---|---|---|
| 5,114,843 | 5/1992 | Rosenblatt et al. | 435/7.21 |
| 5,116,952 | 5/1992 | Martin et al. | 530/399 |
| 5,217,896 | 6/1993 | Kramer et al. | 435/240.27 |
| 5,312,810 | 5/1994 | Wood et al. | 514/12 |

FOREIGN PATENT DOCUMENTS

WO91/10741  7/1991  WIPO ................ C12P 21/06

OTHER PUBLICATIONS

Tashjian, A.H. et al., "Immunochemical identification of parathyroid hormone in non-parathyroid neoplasms associated with hypercalcemia," *J. Exp. Med.*, 119:467–484 (1994).

Suva et al., "A parathyroid hormone–related protein implicated in malignant hypercalcemia: Cloning and expression," *Science*, 237:893–896, (Aug. 1987).

Southby et al., "Immunohistochemical localization of parathyroid hormone–related protein in human breast cancer," *Cancer Res.*, 50:7710–7716 (Oct. 1990).

Burton et al., "Parathyroid hormone related peptide can function as an autocrine growth factor in human renal cell carcinoma," *Biochem. Biophys. Res. Comm.*, 167(3):1134–1138 (Mar. 1990).

Powell et al., "Localization of parathyroid hormone–related protein in breast cancer metastases: Increased incidence in bone compared with other sites," *Cancer Res.*, 51(11):3059–3061 (Jun. 1991).

Yoneda et al., "Occurrence of hypercalcemia and leukocytosis with cachexia in a human squamous cell carcinoma of the maxilla in athymic nude mice: a novel experimental model of three concomitant paraneoplastic syndromes," *J. Clin. Oncol.*, 9(3):468–477 (Mar. 1991).

Abou–Samra et al., "Expression cloning of a common receptor for parathyroid hormone and parathyroid hormone–related peptide from rat osteoblast–like cells: A single receptor stimulates intracellular accumulation of both cAMP and iinositol trisphosphates and increases intracellular free calcium," *Proc. Natl. Acad. Sci. USA*, 89:2732–2736 (Apr. 1992).

Nakai et al., "A synthetic antagonist to laminin inhibits the formation of osteolytic metastases by human melanoma cells in nude mice," *Cancer Res.*, 52:5395–5399 (Oct. 1992).

Sato et al., "Passive immunization with anti–parathyroid hormone–related protein monoclonal antibody markedly prolongs survival time of hypercalcemic nude bearing transplanted human PTHrP–producing tumors," *J. Bone Min. Res.*, 8(7):849–860 (Jul. 1993).

Kohno et al., "The expression of parathyroid hormone–related protein in human breast cancer with skeletal metastases," *Surgery Today, Japan J. Surg.* 4:215–220 (1993).

(List continued on next page.)

*Primary Examiner*—John W. Rollins
*Attorney, Agent, or Firm*—Karl Bozicevic; Fish & Richardson P.C.

[57] ABSTRACT

Materials immunoreactive with parathyroid hormone-related protein (PTH-rp) are used in the invention method to prevent and treat metastasis and cancer cell growth in bone as well as osteolysis and symptomatic sequelae thereof. Humanized antibodies are included in the invention for application of the invention method to human subjects.

14 Claims, 3 Drawing Sheets

OTHER PUBLICATIONS

Sasaki et al., "Growth of metastatic cancer in bone is impaired by inhibitors of bone resorption in vivo," *J. Bone Min. Res.*, 8(1):S139 (Aug. 1993).

Li et al., "Growth factor-like properties of parathyroid hormone-related peptide in transfected rodent cell lines," *Cancer Res.*, 53(13):2980-2986 (Jul. 1993).

Guise et al., "Parathyroid hormone-related protein (PTHrP) expression by breast cancer cells enhance osteolytic bone metastases in vivo" *Breast Cancer Res. Treat.*, 32(supppl): 91 (1994).

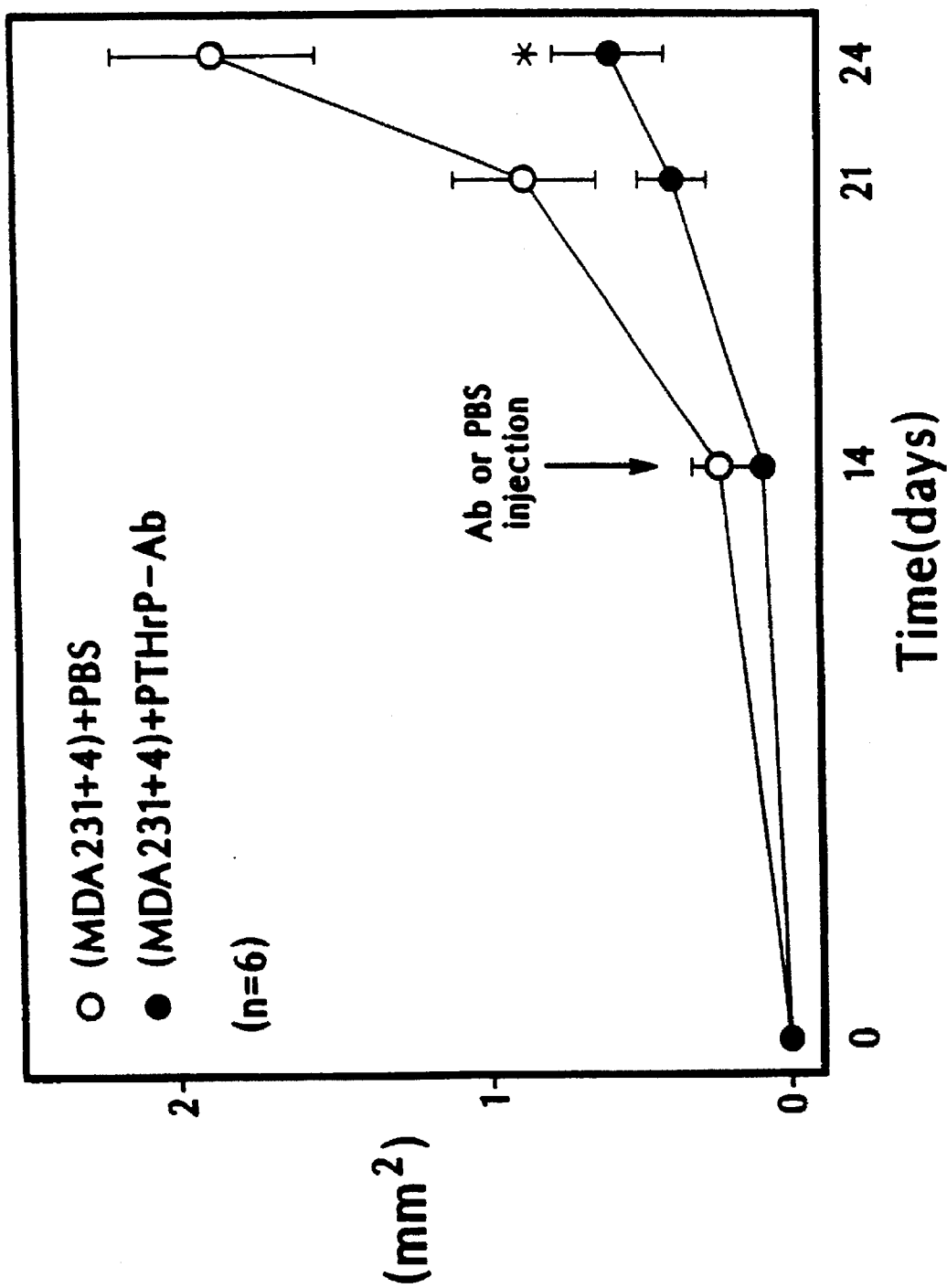

METHOD TO AMELIORATE OSTEOLYSIS AND METASTASIS

Technical Field.

The invention relates to the prevention and treatment of cancer metastasis and bone cancer growth and associated osteolysis mediated by localized production of parathyroid hormone-related protein (PTH-rp). More specifically, the invention concerns use of antibodies and other forms of anti-PTH-rp to alleviate these conditions.

BACKGROUND ART

It has long been understood that morbidity and mortality caused by cancer, especially in view of the fact that surgical techniques are readily available, are due to more-or-less systemic sequelae of the original multiplication of the cancer cells. Metastasis of an original tumor to additional locations, the destruction of target locations as a direct or indirect result of this metastasis, cachexia, hypercalcemia, and other symptomologies characterize the course of the malignancy. The mechanisms whereby these sequelae occur are believed to involve a variety of cytokines, growth factors, and cell adhesion molecules, among other factors.

One such factor which is known to play a role in at least some of these processes is parathyroid hormone-related protein (PTH-rp). Due to its similarity to PTH, it has been recognized as a mediator of humoral hypercalcemia of malignancy (HHM). In this role, PTH-rp secreted by the tumor is circulated through the blood and is associated with hypercalcemia, an index of bone resorption.

PTH-rp has been purified from human lung cancer, breast cancer and renal cell carcinoma. Although PTH-rp was originally found associated with tumor cells, it is also present widely in normal tissue. The gene encoding PTH-rp was cloned and expressed by Suva, L. J. et al. *Science* (1987) 237:893–895. PTH-rp has been shown to bind to PTH receptors (Abou-Samra, A. et al. *Proc Natl Acad Sci USA* (1992) 89:2732–2736) and has activities similar to PTH (Horiuchi, N. et al. *Science* (1987) 23:1566–1568). It has been shown to stimulate adenylate cyclase in renal and bone systems, increase tubular resorption of calcium, decrease renal phosphate uptake and stimulate 1α-hydroxylase.

PTH-rp also has properties that are not shared by PTH, including regulation of placental calcium transport as summarized in a review by Mallette, L. E. *Endocrine Rev* (1991) 12:110–117. Of particular relevance with respect to the invention herein is that PTH-rp has also been associated with the establishment of bone metastasis in breast cancer (Powell, G. J. *Cancer Res* (1991) 51:3059–3061; Southby, J. et al. *Cancer Res* (1990) 50:7710–7716) and has been considered as a possible autocrine factor for some tumors (Burton, P. B. J. et al. *Biochem Biophys Res Com* (1990) 167:1134–1138; Li, X. et al. *Cancer Res* (1993) 53:2980–2986).

Thus, the precise role of PTH-rp in mediating the effects of a primary cancer is not well understood. Not only are there additional factors which also participate in the progress of this condition, the of PTH-rp is believed affected by additional factors such as prolactin, flucocrticoids, epidermal growth factor, TGF-α, TGF-β, estrogen, "stretch," and even extracellular calcium concentration.

Sato, K. et al. *J Bone Min Res* (1993) 8:849–860 describe results obtained in a murine model of HHM wherein the affected mice were administered a monoclonal murine antibody obtained from immortalized spleen cells of mice injected with a peptide representing amino acid positions 1–34 of PTH-rp. Passive immunization resulted in decreases in serum calcium concentration in these hypercalcemia nude mice that had been transplanted with human PTH-rp-producing tumors. The authors suggest that if a human counterpart to this antibody could be obtained, it might be used in treatment where malignancy-associated hypercalcemia is due to PTH-rp. In this model, elevated levels of PTH-rp are maintained in the blood which are, evidently, mitigated by the administration of anti-PTH-rp antibodies. The relevance of this model is verified by the finding of Tashjian, A. H. et al. *J Exp Med* (1964) 119:467 that 15% of 147 hypercalcemia breast cancer patients exhibited no bone metastases.

Hypercalcemia may also be caused by osteolysis of bone through the mediation of osteoclasts (Broadus, A. E. *N Engl J Med* (1988) 319:556–563). In addition, Mundy, G. R. *J Clin Invest* (1988) 82:1–6 describes increased osteoclastic bone resorption in areas surrounding breast cancer metastases and breast cancer cells have been shown to resorb bone directed in vitro by Gutierrez, G. E. et al. *Ballilere Clin Endocrinol Met* (1990) 4:119–138.

Kohno, N. et al. *Proc Natl Acad Sci USA* (1993) 4:215–220 reported studies performed on immobilized sections of surgically removed breast cancers using an anti-PTH-rp antibody also prepared by immunizing mice with the first 34 amino acids of PTH-rp. The antibody bound to 57% of the tumors; it bound to 83% of the tumors derived from patients who developed skeletal metastases but only 38% in those who either developed lung metastases or no metastases at all. These authors conclude that their results suggest that PTH-rp-positive tumors have an affinity to bone.

The present inventors have developed a model of human breast cell cancer metastasis to bone that results in osteolysis. Nakai, M. et al. *Cancer Res* (1992) 52:5395–5399; Sasakai, A. et al. *J Bone Min Res* (1993) 8: (Supplement 1): No. 92. Tumor cells introduced into the left cardiac ventricle of nude mice can be shown to cause osteolytic lesions that can be seen by x-ray examination and that can be confirmed histologically. A375 melanoma cells and the human breast cancer cell line MDA231 have been used in this model. Using this model, it was demonstrated that bone metastasis could be prevented by a synthetic antagonist to laminin.

The present inventors: have also demonstrated that the number of osteolytic lesions is increased by enhancing PTH-rp expression of the MDA231 cells used in the model. Overexpressing clones were obtained by transfecting MDA231 cells with cDNA encoding human prepro PTH-rp; clones having diminished production of this peptide were obtained by transfecting the cell line with an antisense construct. A clone showing elevated expression (100 pM/24 hours) produced 16.3±3.8 lesions radiographically at 3 weeks as compared with the antisense construct which secreted less than 0.3 pM/24 hours which produced only 7.6±0.22 lesions:. No plasma concentrations of PTH-rp were detectable in any of the mice used in these studies; hypercalcemia was minimal and present only in mice harboring the PTH-rp-enhanced MDA231 cells. The present inventors have also shown that PTH-rp concentrations in serum-free media conditioned by MDA231 cells were increased twofold when the cells were cultured on an extracellular matrix produced by bone cells. These results were reported by Guise, T. A. et al. *Breast Cancer Res.trat* (1994) 82:79.

It has now been found that antibodies specific for PTH-rp are affective in inhibiting metastasis and ameliorating the effects of malignant cells localized in bone. This provides an effective pharmacological approach to treatment.

DISCLOSURE OF THE INVENTION

The invention provides a means to treat localized bone effects of metastasized cancer cells, cancers of bone origin, and osteolytic processes in general characterized by localized concentrations of PTH-rp. By administering materials that are immunoreactive with PTH-rp, metastases to the bone can be prevented, growth of cancer cells present in bone can be inhibited, and osteolytic effects can be prevented and treated. Further, the secondary effects of the metastasis, growth, and osteolysis associated with localized phenomena in bone can be mitigated.

Thus, in one aspect, the invention is directed to a method to treat or prevent: metastasis of cancer cells to bone and/or growth of metastasized or bone-originated cancer cells in or on bone which method comprises administering to a subject in need of such treatment an amount of anti-PTH-rp sufficient to treat or prevent said metastasis and/or growth.

In another aspect, the invention is directed to a method to inhibit osteolysis effected by metastasis of cancer cells to bone and/or growth of metastasized or bone-originated cancer cells in or on bone which method comprises administering to a subject in need of such treatment an amount of anti-PTH-rp sufficient to effect said inhibition., In still another aspect, the invention is directed to a method to inhibit osteolysis mediated by bone-localized production of parathyroid hormone-related protein (PTH-rp) which method comprises administering to a subject in need of such treatment an amount of anti-PTH-rp sufficient to effect said inhibition. This method is particularly important in instances of osteoporosis, osteomalacia, renal osteodystrophy or Padgett's Disease.

Another effect of the method of the invention in attacking the primary targets described above is the amelioration of secondary symptomologies. These include pain, neural compression, hypercalcemia, risk of pathologic fractures, cachexia and decreased survival pronosis.

In still other aspects, the invention is directed to compositions useful in the methods of the invention and to methods to identify and treat subjects who would benefit from the methods of invention treatment as well as methods to obtain antibodies useful in the methods of the invention.

BRIEF DESCRIPTION OF THE DRAWINGS

FIG. 3 is a graph showing the effect of administering anti-PTH-rp antibodies on the total area shown to be associated with bond lesions by x-ray diagnosis in tumor-bearing mice.

Modes of Carrying Out the Invention

Figure 1:
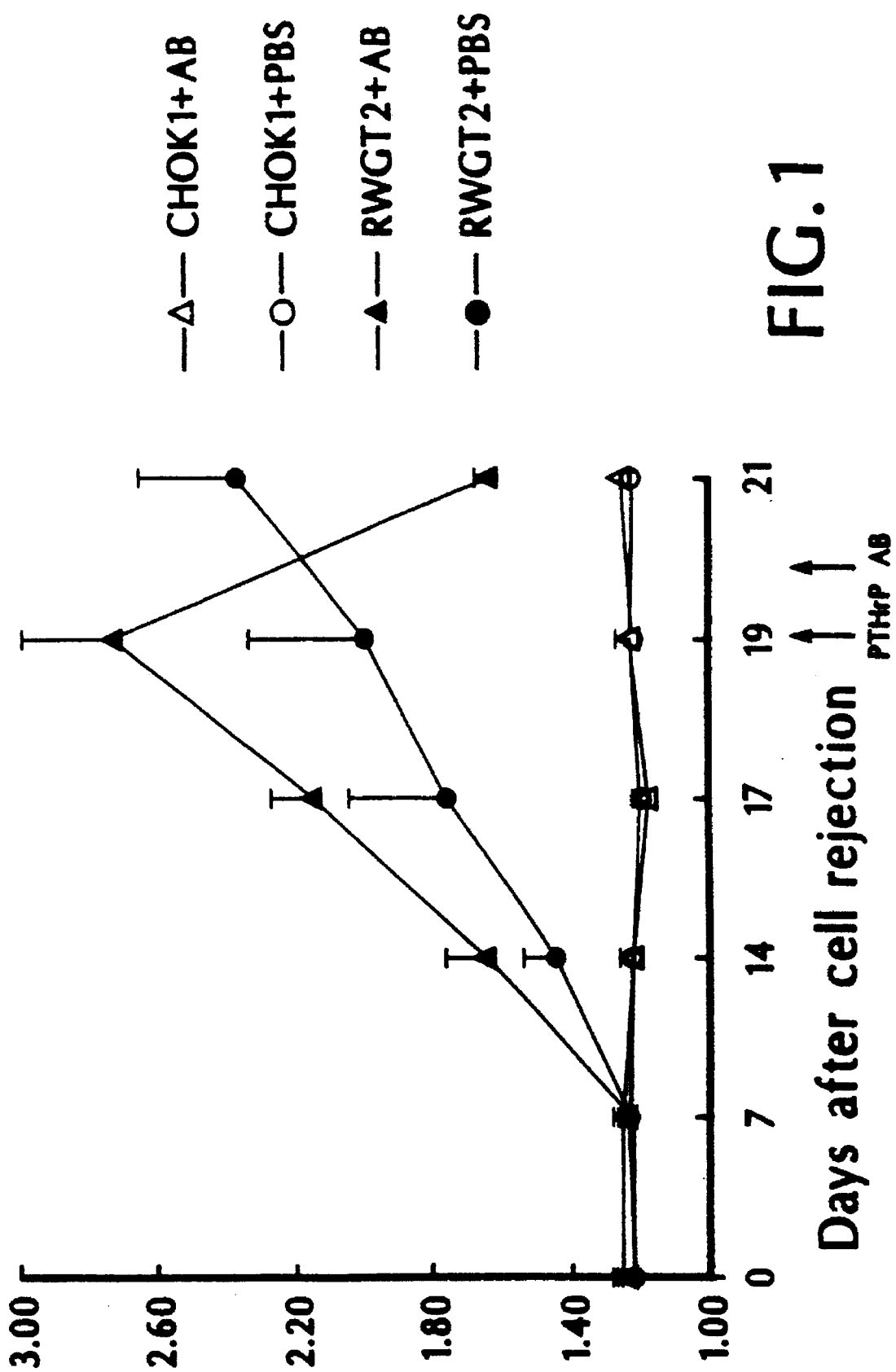
FIG. 1 is a graph that shows the effect of monoclonal antibodies specific for PTH-rp on serum calcium levels in tumor-bearing mice.

All of the invention methods and compositions employ substances immunoreactive or immunospecific for PTH-rp. Substances that are immunoreactive with PTH-rp are generally designated "anti-PTH-rp."

As used herein, the term "anti-PTH-rp" refers to antibodies immunoreactive with PTH-rp and antibody analogs, substitutes and fragments as are known in the art. It is preferred that the anti-PTH-rp also be immunospecific—i.e., not substantially cross-reactive with related materials such as PTH. However, anti-PTH-rp is effective in the method of the invention as long as it is immunoreactive PTH-rp per se.

Examples of art-known analogs, fragments and substitutes for antibodies include fragments such as Fab, Fab', and F(ab')$_2$ fragments as well as singe-chain forms designated F$_v$ fragments obtained recombinantly by fusing the genes encoding the light- and heavy-chain variable regions. Antibodies can be monoclonal or polyclonal and can be those produced in response to administration of an antigen without modification, or, since recombinant techniques have become available, modifications to these antibodies are also possible. For example, also included within anti-PTH-rp are chimeric antibodies which represent regions of amino acid sequences derived from different species as well as modified forms of antibodies generated by one species that have been altered so as to resemble those of another species without altering the antigen specificity. A particularly preferred embodiment of the anti-PTH-rp of the invention includes antibodies produced in response to administration of PTH-rp to transgenic mice whose immune systems have been modified so that human antibodies can be generated.

Anti-PTH-rp can be prepared in a variety of ways. In one approach, a suitable immunogen, such as PTH-rp or a subunit thereof is administered to a vertebrate capable of an immune response to the immunogen. Particularly preferred subunits of PTH-rp included those in the N-terminal region, in particular positions 1–34. The PTH-rp or subunit used as immunogen should include epitopes characteristic of the particular species PTH-rp for which antibodies are desired. Suitable polyclonal antisera from the immunized animals could be used; however, it is preferred to obtain monoclonal preparations that are reproducible and readily prepared. Such monoclonal preparations can be obtained by immortalizing the antibody-producing cells of the immunized animal and screening for the appropriate immunoreactivity. Immunospecificity can also be ascertained by screening out those hybridomas that secrete antibodies that are cross-reactive with closely related materials such as PTH.

The resulting antibodies can be used per se or fragments of these antibodies can be prepared using standard proteolytic techniques to provide the Fab, Fab', and F(ab')$_2$ fragments. Alternatively, the genes encoding the antibodies may be isolated, for example from the hybridoma, and manipulated to alter the characteristics of the antibody. Using the isolated genes, F$_v$ units can be constructed which contain the light- and heavy-chain variable regions covalently linked in a single peptide unit.

Since it is preferable that the antibodies to be administered have minimal immunogenicity in the subject to be treated, the antibodies may be manipulated to provide the characteristics of the species of the subject in the nonbinding portions. Construction of chimeric antibodies that contain the constant regions of the desired species is well known; further, techniques are available in the art to modify the antibody primary sequence so as to correspond more closely to the species to be treated.

A number of approaches to do this, for example, to humanize antibodies are known. In general, these involve engineering the variable region-encoding portions of the gene so that the complementarity-determining regions (CDRs) are left intact while the framework (FR) regions are modified to match those of the desired species. A particularly preferred way to obtain antibodies immunoreactive with PTH-rp and having human characteristics is through immunization of a transgenic animal which animal responds to administration of antigen by producing human antibodies rather than antibodies with the characteristics of endogenous immunoglobulins. Such transgenic animals are described, for example, in PCT Application WO91/10741.

The appropriate antibodies or other forms of anti-PTH-rp are formulated for administration in a manner customary for administration of such materials. Typical formulations are those provided in *Remington's Pharmaceutical Sciences*, latest: edition, Mack Publishing Company, Easton, Pa. Preferably, the anti-PTH-rp is administered by injection, including intramuscular, intravenous, subcutaneous or peritoneal injection. However, other modes of administration may also be used provided means are available to permit the anti-PTH-rp to enter the systemic circulation, such as transmucosal or transdermal formulations which can be applied as suppositories, skin patches, or intranasally. Any suitable formulation which effects the transfer of the anti-PTH-rp to the bloodstream or locally to the bone may properly be used.

As described herein, the subjects who would benefit from administration of the anti-PTH-rp are those who show metastasis of cancer cells to bone or the growth of cancer cells in bone or osteolysis. These patients may or may not have elevated levels of PTH-rp circulating in the blood, unlike those subjects whose hypercalcemia is mediated by the humoral system.

This distinction between HHM and the metastasis/osteolysis that is the target of the anti-PTH-rp treatment described herein is clearly demonstrated in the murine model system described by the present inventors in Nakai et al. (supra). Two tumor cell lines were used in this model: RWGT-2 which is a human squamous cell carcinoma of the lung that produces large amounts of PTH-rp in culture (251±8 pM) and MDA231, the human breast adenocarcinoma described above that produces low amounts in vitro (3.1±0.3 pM). The cultured tumor cells were inoculated by intramuscular ($10^7$ cells) or intracardiac injection ($10^5$ cells) into athymic nude mice. The levels of calcium ion in blood and of PTH-rp in plasma were measured, along with obtaining skeletal radiographs and bone histology.

Mice inoculated intramuscularly with either cell line developed local tumors in three weeks without metastases. Mice bearing RWGT-2 developed hypercalcemia (2.44±0.16 mM calcium) with increased PTH-rp (11.8±2.2 pM). Mice bearing MDA231 remained normal calcemic (1.22±0.03 mM) and PTH-rp was not increased in the plasma (0.69±0.17 pM). Osteoclastic bone resorption occurred in the RWGT-2-bearing mice, but not in MDA231-bearing mice.

On the other hand, mice inoculated in the left ventricle with either cell line developed osteolytic lesions in 4 weeks. MDA231-bearing mice remained normal calcemic (1.22±0.03 mM) as did mice bearing RWGT-2 (1.45±0.19 mM). PTH-rp concentration in the plasma was not increased in the MDA231-bearing mice (0.88±0.15 pM) and only slightly increased in RWGT-2-bearing mice (2.75±2.68 pM). However, tumor was present adjacent to areas of increased osteoclastic bone resorption in both groups.

Thus it is clear that. PTH-rp causes different syndromes depending on where it is produced; when produced by tumors at a distant site from bone at high levels (RWGT-2), plasma PTH-rp is increased and hypercalcemia occurs without metastatic bone disease. When produced locally by tumor cells in bone (MDA231) localized bone destruction with or without hypercalcemia occurs without necessarily an increase in circulating PTH-rp. Thus, the syndrome addressed by the method of the present invention is different from HHM.

The following examples are intended to illustrate but not to limit the invention.

EXAMPLE 1

Effect of PTH-rp Monoclonal Antibody on Calcium Levels

The osteolytic/metastatic model of Nakai, M. et al. *Cancer Res* (1992) 52:5395–5399 was used. Mice were injected in the left ventricle with either CHOK-1 cells or with the squamous cancer cells RWGT-2 on day 0. The cells ($1\times10^5$) were suspended in 0.1 ml PBS and injected with a 7-gauge needle into the left cardiac ventricle with the mice under anesthesia with 0.05 mg/g pentobarbital. On days 19 and 20 the mice received either 0.3 ml PBS or 0.3 ml anti-PTH-rp (1–34) monoclonal antibodies (Sato et al. *J Bone Min Res* (1993) 8:849–860) subcutaneously.

Calcium levels were measured at days 0, 7, 14, 7, 19 and 21. For the measurement, the mice were anesthetized and calcium ion was determined using a Ciba-Corning calcium pH analyzer (Model 634, Corning, Medfield, Ma.) as described by Yoneda, Y. et al. *J Clin Oncol* (1991) 9:468–477.

The results are shown in FIG. 1. As shown, the control mice implanted with CHOK-1 Cells maintain normal calcium levels. Mice bearing RWGT-2 show continuously increasing calcium levels (solid circles) when only PBS is administered while administration of the anti-PTH-rp dramatically lowers the calcium levels in the blood of mice receiving antibody (solid triangles).

EXAMPLE 2

Effect of Anti-PTH-rp on Bone Resorption Stimulated by Various Agents

Figure 2:
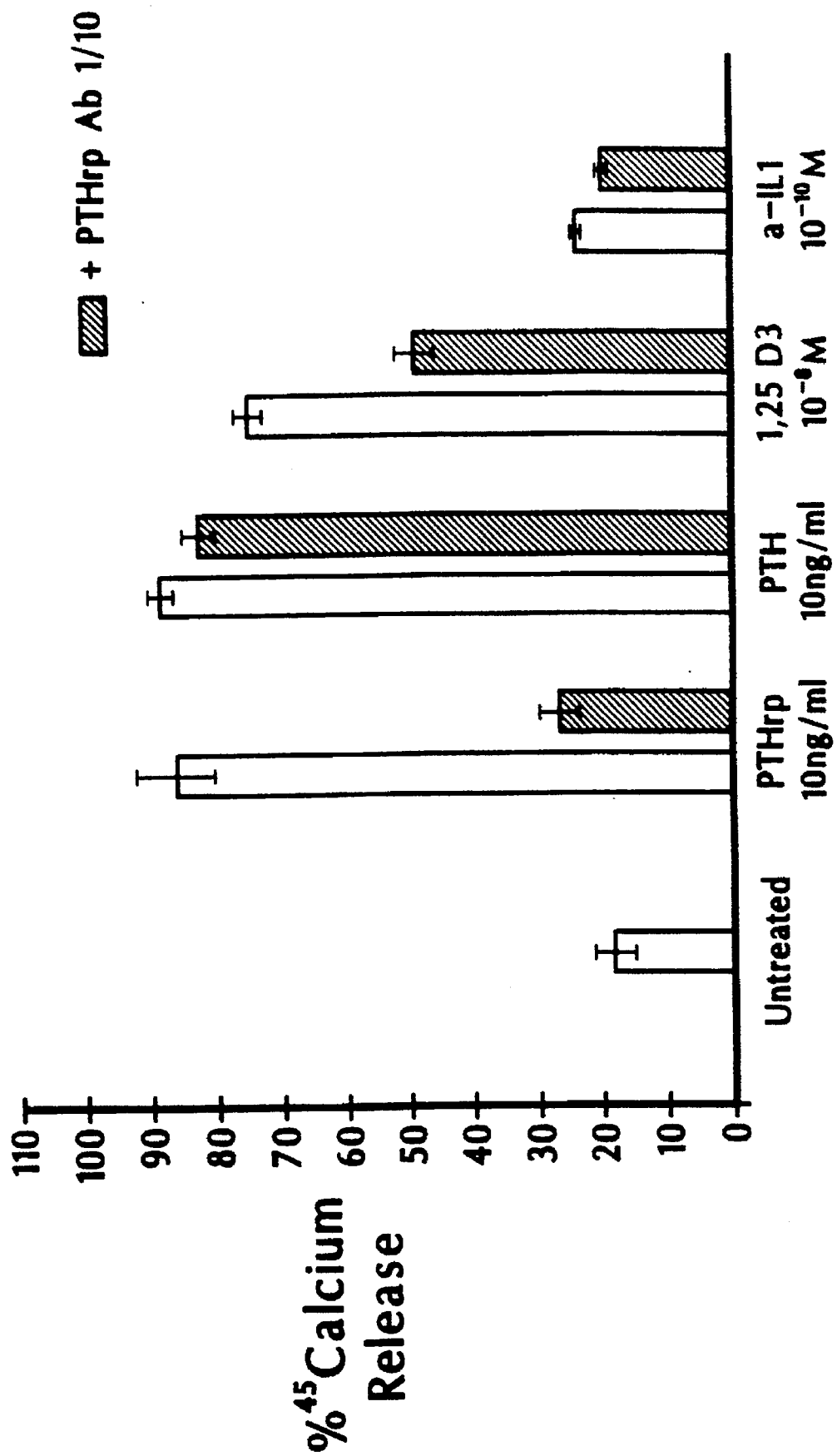
FIG. 2 is a graph showing the effect of monoclonal antibodies specific for PTH-rp on calcium release in bone resorption stimulated by PTH-rp, PTH, or IL-1.

In this example, the percentage of labeled calcium ($^{45}$Ca) from fetal rat long bone was used as a measure of bone resorption. To label the bones, pregnant female rats were injected with 75 mg of labeled calcium salt subcutaneously every three days. The embryos were harvested and the long bones obtained from the fetuses. The bones were cultured in standard media for 120 hours in the presence or absence of various putative bone resorption stimulation factors and in the presence and absence of the anti-PTH-rp (1–34) antibody used in Example 1. The results are shown in FIG. 2.

As shown, untreated bones released roughly 20% of the labeled calcium into the medium over the 120-hour time frame. The addition of 10 ng/ml of PTH-rp to the culture medium results in release of almost 90% of labeled calcium; however, addition of anti-PTH-rp antibodies diminishes this to roughly 30%. Addition of 10 mg/ml PTH itself to the medium also results in almost 90% release of the calcium indicator of bone resorption but the antibody is sufficiently immunospecific to PTH-rp that there is essentially no effect by virtue of the presence of this antibody. The antibody also appeared to diminish the calcium release stimulated by 125 D-3 present at $10^{-8}$ M, however, these results could not be repeated. The addition of αIL-1 at $10^{-10}$ M had little effect on calcium release and the addition of the antibody was also without effect.

EXAMPLE 3

Effect of Anti-PTH-rp on Long Bone Lesions

The model set forth in Example 1 was used except that MDA231+4 cells were injected into the left ventricle on day 0. On day 14, anti-PTH-rp (1–34) or PBS was injected as described in Example 1. The area of bone lesions was estimated on radiographs; the mice are anesthetized deeply, laid down in prone position against the films (22×27 cm X-O Mart AR Kodak, Rochester, N.Y.) and exposed with an x-ray at 35 kvp for 6 seconds using a Faxtron Radiographic Inspection Unit (Model 8050-020, Field Emission Corporation, Inc., McMinnville, Oreg). Films are developed using an RPX-O Mart Processor (Model M8B, Kodak). All radiographs are evaluated extensively by three different individuals. Metastatic foci, recognized as demarcated radiolucid lesions in bones, are enumerated. At the end of the experiment, the mice are sacrificed and bones are fixed in buffered 10% formalin and decalcified to confirm the presence of metastatic tumor and to examine the relationship between tumor and the related bones.

The results are shown in FIG. 3. As indicated, the total lesion area is diminished when anti-PTH-rp is administered and is statistically significantly decreased at day 24.

EXAMPLE 4

Osteoporosis Model

Ovariectomized female rats are used as a model of osteoporosis. Bone loss is quite rapid: in the tibial metaphysis, 80% of the secondary spongiosa is lost over 3 months; loss in the vertebrae is only slightly slower. The rats may be studied in the acute phase of bone loss following ovariectomy or some months later, depending on whether the aim is to block bone loss or to stimulate recovery of lost bone.

One week after ovariectomy or sham surgery, 250-gram Sprague-Dawley rats are given either PBS, control antibodies, anti-PTH-rp (1–34) or estrogen over a period of 28 days with the injections administered under methoxyflurane anesthesia. Prior to sacrifice, rats are administered single doses of tetracycline and then demeoloyoyline in order to assess rates of mineralization. After euthanasia, the tibia and lumbar vertebrae are removed, fixed and processed for histomorphometric evaluation of decalcified and undecalcified sections.

Bone mineral density and assessment of bone mass are determined by dual energy x-ray absorptiometry. The animals administered anti-PTH-rp show a decrease in bone loss.

We claim:

1. A method of treating growth of metastasized cancer cells on bone which method comprises administering to a subject in need of such treatment an amount of anti-PTH-rp sufficient to treat said growth.

2. The method of claim 1 wherein said cancer cells have metastasized from a primary site other than bone.

3. The method of claim 2 wherein said primary site is selected from the group consisting of breast, lung, kidney, head/neck, prostate, pancreas, skin, thyroid, testis, liver, urothelium, endometrium, cervix, esophagus, blood, and lymphoid tissues.

4. The method of claim 1 wherein said cancer cells are of bone origin.

5. The method of claim 1 wherein said method further results in ameliorating a symptom associated with said cancer cell growth.

6. The method off claim 5 wherein said symptom is selected from the group consisting of that wherein said subject is suffering from pain and said treating alleviates said pain;

that wherein said subject is at risk for neural compression and said treating avoids or alleviates said compression;

that wherein said subject is hypercalcemia and said treating results in amelioration of said hypercalcemia;

that wherein said subject is at risk for mortality and said treating lengthens survival time;

that wherein said subject is at risk for pathologic fractures and said treating lessens said risk; and that wherein said subject is cachexic and said treating ameliorates said cachexia; and combinations of the foregoing.

7. The method of claim wherein said cancer cells are selected from the group consisting of squamous cell carcinoma cells, adenocarcinoma cells, melanoma cells, osteosarcoma cells, and hematologic cancer cells.

8. A method to preventing metastasis of cancer cells to bone which method comprises administering to a subject in need of such an amount of anti-PTH-rp sufficient to prevent said metastasis.

9. The method of claim 8 wherein said cancer cells are prevented from metastasizing from a primary site other than bone.

10. The method of claim 9 wherein said primary site is selected from the group consisting of breast, lung, kidney, head/neck, prostate, pancreas, skin, thyroid, testis, liver, urothelium, endometrium, cervix, esophagus, blood, and lymphoid tissues.

11. The method of claim 8 wherein said cancer cells are of bone origin.

12. The method of claim 8 wherein said method further results in ameliorating a symptom associated with said metastasis.

13. The method of claim 12 wherein said symptom is selected from the group consisting of that wherein said subject is suffering from pain and said preventing alleviates said pain;

that wherein said subject is at risk for neural compression and said preventing avoids or alleviates said compression;

that wherein said subject is hypercalcemia and said preventing results in amelioration of said hypercalcemia;

that wherein said subject is at risk for mortality and said preventing lengthens survival time;

that wherein said subject is at risk for pathologic fractures and said preventing lessens said risk; and that wherein said subject is cachexic and said preventing ameliorates said cachexia; and combines of the foregoing.

14. The method of claim 8 wherein said cancer cells are selected from the group consisting of squamous cell carcinoma cells, adenocarcinoma cells, melanoma cells, osteosarcoma cells, and hematologic cancer cells.

* * * * *